(12) United States Patent
Bates

(10) Patent No.: US 7,964,407 B2
(45) Date of Patent: Jun. 21, 2011

(54) METHODS OF MARKING PRODUCTS USING NATURAL MATERIALS HAVING GENETICALLY CONTROLLED MICROMORPHOLOGICAL STRUCTURES AS MARKERS

(76) Inventor: Lynn S. Bates, Manhattan, KS (US)

( * ) Notice: Subject to any disclaimer, the term of this patent is extended or adjusted under 35 U.S.C. 154(b) by 1963 days.

(21) Appl. No.: 10/897,781

(22) Filed: Jul. 21, 2004

(65) Prior Publication Data

US 2006/0019006 A1    Jan. 26, 2006

(51) Int. Cl.
*G01N 37/00* (2006.01)
(52) U.S. Cl. .......................... 436/56; 436/164; 436/172
(58) Field of Classification Search .................. 436/56, 436/63, 172, 501, 164; 435/7.1
See application file for complete search history.

(56) References Cited

U.S. PATENT DOCUMENTS

| | | | |
|---|---|---|---|
| 4,421,858 A * | 12/1983 | Jackson | 436/20 |
| 5,753,511 A | 5/1998 | Selinfreund | |
| 5,776,713 A | 7/1998 | Garner et al. | |
| 5,846,830 A | 12/1998 | Demello et al. | |
| 5,897,797 A | 4/1999 | Drouillard et al. | |
| 5,942,444 A | 8/1999 | Riittenburg et al. | |
| 6,068,981 A * | 5/2000 | Rittenburg et al. | 435/7.1 |
| 6,180,354 B1 * | 1/2001 | Singh et al. | 435/7.1 |
| 6,232,124 B1 | 5/2001 | Selinfreund | |
| 6,406,725 B1 * | 6/2002 | Taylor | 426/87 |
| 6,461,607 B1 * | 10/2002 | Farmer | 424/93.45 |
| 6,649,414 B1 * | 11/2003 | Chandler et al. | 436/63 |
| 7,163,744 B2 * | 1/2007 | Nightingale et al. | 428/397 |
| 2002/0173042 A1 * | 11/2002 | Oolman et al. | 436/56 |
| 2005/0002963 A1 * | 1/2005 | Beckett et al. | 424/195.15 |

OTHER PUBLICATIONS

Baker et al., Trends in Food Science and Technology Sep. 1996, vol. 7 pp. 279-284.*
Wolf, Lauren, "Newscripts: Probiotic Allergy Relief, Fighting Crime with Pollen," CEN-Online.org, p. 88, Aug. 18, 2008.
Bates, Lynn S., Internal Standards for Basic Amino Acid Analyses, Analytical Biochemistry 41, pp. 158-161 (1971).
Bates, L.S., Micromorphological Markers for Transgressive Segregation Studies of Intergeneric Barley Hybridization, Session X. Intergeneric Crosses, $F_1$ Hybrids, Cytology, pp. 814-820 (1982).
AOAC Manual (10th Ed. 1965), p. 350, Sec. 23.021, "Soybean Flour—Qualitative Test."
Structure & Composition of Foods, Winton & Winton (1932), p. 512, "Soybean."
Canada Department of Agriculture, "After Microscopical Analysis of Feedstuffs," Figures 1 and 2.
Pearson, "The Chemical Analysis of Foods," p. 241 (1976).

* cited by examiner

*Primary Examiner* — Jill Warden
*Assistant Examiner* — Dwan A Gerido
(74) *Attorney, Agent, or Firm* — Jeffrey L. Thompson; Thompson & Thompson, P.A.

(57) ABSTRACT

Methods of marking products and of determining the origin or authenticity of marked products are provided that use a variety of natural materials as markers. The natural materials have unique genetically controlled micromorphological structures that can be identified using enhanced visualization techniques. For example, cellulosic plant materials, sporopollenin and diatoms can be used as the natural materials. The natural materials are added to products at sufficiently low levels so as not to have any significant effect on the products other than serving as markers. Dyes and reactants can be added to the natural materials to provide secondary markers. The secondary markers can be vacuum infused into hollow interior spaces of the materials, or placed in surface voids of the materials to remain secured in the marker structures until examined. Sub-cellular particles or heat sensitive molecules can also be used to provide a molecular thermometer for the markers.

34 Claims, 3 Drawing Sheets

US 7,964,407 B2

METHODS OF MARKING PRODUCTS USING NATURAL MATERIALS HAVING GENETICALLY CONTROLLED MICROMORPHOLOGICAL STRUCTURES AS MARKERS

FIELD OF THE INVENTION

The present invention relates to the marking of products to establish their identity and source. In particular, the present invention relates to the use of various natural materials having genetically controlled micromorphological structures as markers for the identification of processed foods, food ingredients, and various other products unrelated to the marker materials.

BACKGROUND OF THE INVENTION

The identification of processed foods has a long history. For marketing purposes, specific brand names and logos have always informed consumers of food quality. Consumer confidence was maintained on a solid basis of brand integrity. When the Food and Drug Administration ("FDA") was created, it added legal requirements for labeling of foods for uniformity and consumer protection. The latest labeling law requires additional portion and nutritional information. But what has long been missing for both manufacturer and consumer confidence has been the traceability of ingredients and processed foods through the entire food system from harvest to consumer.

Purchasing department paper trails have provided some traceability, particularly from harvest to processor, but once the food or ingredient has been processed, there have been no methods available to identify one processing site or source from another. With the current concepts of liability and insurance claims, the food manufacturing industries need to be able to identify their products in the marketplace in the absence of any labeling or other identification. It is particularly important to be able to identify small quantities of returned food items that may or may not be in their original packaging, which may or may not be correctly identified by the person returning the item(s), or for any other of many reasons. The need for specific markers that can trace the identity of a food back to its original processing location is becoming a critical new requirement for food manufacturers.

Markers need to trace a wide range of processed foods, some of which cannot be readily adapted to having materials added to them. In some cases, sub-cellular markers may have to be used to provide identity. In others, cellular or multi-cellular materials may be used. Many spices and preservatives can be markers themselves, as well as in conjunction with morphological markers to provide additional specificity for product identifications. Sometimes a completed food item has components from several sources. Markers of different kinds are needed to identify the manufacturers of buns and meat patties that become part of a completed food product or system. The similarity of baked buns, for example, makes it critical for a supplier of buns to be able to identify their products from those of another supplier of buns used in the same restaurant or outlet. It is particularly critical when liability must be determined for foreign material reportedly found in a bun where two suppliers are used at the same location. In addition, the markers used in buns cannot confound those used in meats or condiments, and so forth.

SUMMARY OF THE INVENTION

An object of the present invention is to provide a method of marking food products that solves the problems with the prior art discussed above, and that allows identification of a food product after the point of sale or return of a specific food item.

It is a further object of the present invention to provide a method of marking food products that uses natural cellulosic material and other natural polymers and materials that are non-allergenic, that can be matched to the characteristics and functional properties of the food product, and that are resistant to visible changes induced by mechanical, physical or chemical processing variables during manufacturing of the food product.

It is a further object of the present invention to provide a method of marking food and other products that offers a large number of distinct markers that can be identified rapidly using enhanced visualization techniques.

It is a further object of the present invention to provide a clearinghouse for providing and/or tracking a large number of unique markers for food and other products.

To achieve these and other objects of the present invention, the Applicant has developed methods of marking products and of determining the origin or authenticity of products that use a variety of natural materials as markers. The natural materials have unique genetically controlled micromorphological structures that can be identified using enhanced visualization techniques. For example, cellulosic plant materials, sporopollenin and diatoms can be used as the natural materials. The natural materials are added to the products to be marked at sufficiently low levels so as not to have any significant effect on the marked products other than to serve as markers. Dyes and reactants, particularly chromophoric reactants, can be added to the natural materials to provide secondary markers. The secondary markers can be vacuum infused into hollow interior spaces of the natural materials, or placed in surface voids of the natural materials to remain secured in the marker structures until examined. Sub-cellular particles, such as starch granules, and heat sensitive molecules, such as enzymes, can also be used to provide a molecular thermometer for the markers. The marked products will generally be food products, but can also be various other products unrelated to the marker materials.

According to a broad aspect of the present invention, a method of marking products is provided, comprising the steps of: selecting a natural material having a unique genetically controlled micromorphological structure that can be identified using an enhanced visualization technique; and adding the natural material to a product unrelated to the natural material at a sufficiently low level so as not to have any significant effect on the product other than to serve as a marker for the product.

According to another broad aspect of the present invention, a method of providing a plurality of different markers for food products is disclosed, comprising the steps of: providing at least one natural material having a unique genetically controlled micromorphological structure; providing at least one secondary marker selected from the group consisting of dyes and reactants; and making a plurality of different combinations of the at least one natural material and the at least one secondary marker to provide a plurality of different markers for food products.

According to another broad aspect of the present invention, a method of determining an origin or authenticity of a marked product is provided, comprising the steps of: obtaining a sample of the marked product; determining by use of enhanced visualization whether the sample contains a particular natural material having a unique genetically controlled micromorphological structure at a sufficiently low level so as not to have any significant effect on the marked product other than to serve as a marker for the product; and comparing the detected natural material with known markers to determine the origin or authenticity of the marked product.

Numerous other objects of the present invention will be apparent to those skilled in this art from the following description wherein there is shown and described exemplary embodiments of the present invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the invention is made with reference to the accompanying drawings. In the drawings.

DETAILED DESCRIPTION OF THE INVENTION

Figure 1:
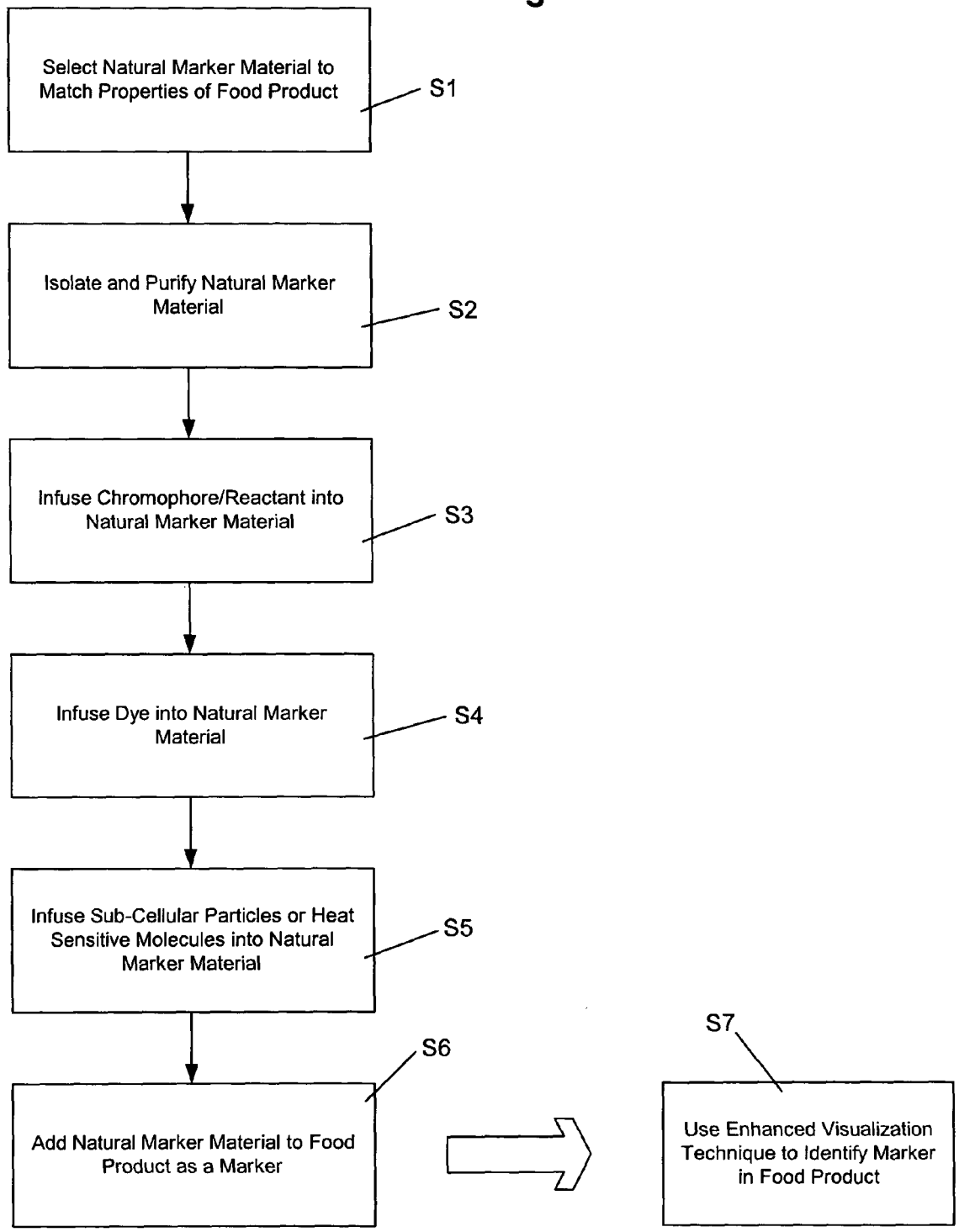
FIG. 1 is a flow chart of a process for marking food products using natural marker materials according to the present invention.

A detailed description of the preferred embodiments of the present invention is provided herein. It is, however, to be understood that the disclosed embodiments are merely illustrative of the invention, which may be embodied in various forms. Therefore, specific structural and functional details disclosed herein are not to be interpreted as limiting, but merely as a basis for the claims and as a representative basis for teaching one skilled in the art to employ the process of the present invention.

Overview

The wide range of diverse life forms on Earth produce an equally wide range of unique cells and sub-cellular particles that can be harvested and processed. These cells and particles are genetically controlled and thus remain the same from year to year in each new generation of a particular species. Many of these cells and particles are also resistant to any significant modifications caused by the physical forces and chemical changes common to food processing. Thus, there are many cells and particles available to be used as unique identifying tags or markers for the branding or marking of processed foods and ingredients for processed foods (collectively referred to as "food products") and various other manmade products. Most of the available marker materials are going to be fiber or non-digestible materials.

The first type of markers are those materials that are environmentally stable, resistant to processing, Generally Recognized As Safe ("GRAS"), and common to the type of food product being marked. For baked products, a very specific cereal cell type, a cellulosic fiber fraction, for example, can be isolated and used to mark all the baked products from a single bakery or manufacturer. The fibrous cell fraction could be included in the fiber component for labeling purposes. The unique specificity of these markers would allow them to be used at very low levels below any taste threshold in the baked good.

The second type of markers are those materials that fit the above criteria but are specific fibrous cell types from non-traditional bakery food ingredients. These markers would make the identification more specific for a particular baked product, but might not be able to be included in all the baked goods from a particular bakery. The identity of the marker source on the label would reveal more about the marker than one from a more traditional bakery ingredient. Sub-cellular markers could also be isolated and included as part of the fiber portion of the label. The presence of a cellular and/or a secondary sub-cellular fraction would offer additional identification probabilities for baked products. If used at sufficiently low levels, the marker source may not even need to be identified on the label.

In many cases, the cells and particles of interests are by-products or sub-products of food processing and have become feed ingredients. These are available in large quantities but may have one or more characteristics that cause them to be removed. For example, they may be highly fibrous, tough, hard, colored or undesirable for whatever other reason and are removed to enhance the value of the food. However, many of these materials can be further processed to make isolates that are unique and GRAS. In other cases, the unique tag or marker may be found in a wild relative of one of our common crop plants that is GRAS but perhaps lacks the desirable characteristics of its domestic counterpart for agronomic or processing reasons. These too can be grown, harvested and the unique marker(s) processed and concentrated for tracing processed foods. Unique markers may also be found in non-traditional portions of a food source, such as pollen, that can be processed to create totally unique markers. Of course the pollen must be purified to remove surface antigens and allergens before it can be used as a marker for food products.

Markers for ground meat are more difficult than for plant-based foodstuffs. The major difficulty is the lack of cell types associated with meat that are unique enough to be used for tracing products. Current law would permit marking via flavoring mixtures. Pure ground meat cannot normally be marked. However, natural cellulosic markers can be used in meats and other animal-based foods due to their low inclusion rates. Cellulose is not produced by animals so a meat product marked with a cellulosic material (e.g., less than one ppm) should be an excellent marker solution.

The present invention can also be used to mark milk, ice cream, cheese, yogurt, and so forth. These are all particulate or emulsified materials for which an insoluble marker would be applicable. The marking technique of the present invention would probably not be suitable for clear liquids, such as soft drinks, wines, fruit drinks, and so forth, because the particulates used for marking would tend to settle out of the solution and cause an undesirable appearance. However, cloudy drinks, such as tea mixtures, could be marked with a low inclusion rate particulate marker because they have microparticulates in them as part of the tea.

Natural Marker Materials

The present invention uses the natural cellular characteristics of certain materials that have unique genetically controlled micromorphological structures that can be identified rapidly in several ways with the aid of a microscope or other enhanced visualization methods. The natural materials are non-allergenic and can be selected to match the characteristics and functional properties of a particular food product or other product being marked. These can be subsequently built upon or in to produce added specificity to the natural genetic micromorphological marker. The natural marker materials will be selected to be resistant to visible changes induced by mechanical, physical or chemical processing variables during manufacturing of the marked product. The step of selecting a natural marker material to match the properties of a food product in which it will be used is shown as step S1 in FIG. 1.

The natural marker materials can be obtained from a variety of sources, including natural cellulosic plant materials, sporopollenin, and diatoms. In one embodiment, the natural marker material is cellulosic plant material comprising hollow plant fibers. For example, the hollow plant fibers can be sycamore seed fibers, oat trichomes, milkweed pods, capok, alfalfa trichomes, and so forth. Other sources of plant fibers, such as weed seeds, leaves and cockle burrs, can also be used. Plant appendages, such as plant hairs and the like, provide particularly good sources of genetically controlled micromorphological structures that can be identified rapidly under a microscope.

The natural cellulosic plant material will preferably have either hollow interior spaces, as in the hollow plant fibers described above, or surface voids or pits (collectively referred to herein as "surface voids"). As explained below, secondary markers can be placed in the hollow interior spaces and surface voids of the natural cellulosic material to create specificity and enhanced visibility. The natural marker material is then added to food products, as indicated in step S6 in FIG. 1, at sufficiently low levels so as not to have any significant effect on the food product other than to serve as a marker for the food product.

The purification of such a wide range of materials is not possible with a single type of method. Plant cell isolation has no general method. Each type of cell requires a different method. Leaf cells, pollen, stem cells, and seed tissues will all be different. The methods to isolate these fractions are available within the confines of known food processing techniques. Once the desired plant material is isolated, it may be necessary to grind the plant fibers to obtain the desired particulate size for the markers. The step of isolating and purifying the natural marker material is shown as step S2 in FIG. 1.

Pollen and allergenic particles can also be used as markers and are of particular interest because of their tough stable exine layer and their unique structures. The pollen can be cleaned of the surface antigens and the active enzymes in the interior leaving only the exine for identification purposes. Only the exine will generally be used for the marker material because it is easily identified and formed of sporopollenin, which is a relatively inert polymer that is environmentally stable and thus not modified by most food processing. The specific pollen source will determine the exact purification technique. The purification process will involve a combination of enzymatic, acidic and/or alkaline hydrolysis, flotation, decantation, centrifugation, drying and agglomerated particle reduction.

Diatoms can also be used as the natural materials for the markers of the present invention because they have silicified skeletons with a unique genetically controlled micromorphological structure that can be identified easily under a microscope. Diatoms are normally not be preferred for marking food products because they tend to impart an undesirable grittiness to the food that can be felt by the mouth. However, diatoms can be particularly useful for marking food packaging and various other nonfood products. The silicified skeletons of the diatoms are the product of the genetics of a particular organism and thus a parallel situation to the cellulosic plant material and sporopollenin materials described above.

Secondary Markers

The natural marker materials described above can be modified using dyes and/or reactants and particularly chromophoric reactants to produce a secondary marker effect. The secondary markers will be added to the unique structures of the natural marker materials to enhance the visibility of the markers, as well as to increase the number of possible marker combinations, thereby creating specificity where multiple markers are required. The step of adding reactants into the natural marker material is shown as step S3 in FIG. 1, and the step of infusing dyes or other colorants into the natural marker material is shown as step S4.

The secondary marker can be in the form of one or more reactants, particularly chromophoric reactants, that are added to the natural cellulosic markers. These are compounds that will react with specific reagents to produce color many times more intense than that of dyes or other colorants. An example of the use of a chromophore that is part of the food is the use of iron salts. The presence of iron can be detected readily by converting it to an indigo blue. When the indigo blue is not in a cell where natural iron would be found, and the blue is in a specific micromorphological marker, the product can be clearly confirmed to be the marker. Copper is another example of a metallic ion that is commonly found in foods and that can be determined to be located in a particular structure rather than distributed throughout the food matrix.

The secondary marker can also be in the form of a dye or other colored compound added to the natural cellulosic markers. A dye molecule, either a natural dye like an anthocyanin or a synthetic dye like an FDA Red 40, entrapped in the specific structure of a micromorphological marker adds to the specificity of the marker and enhances its visual characteristics. The more specific layers that can be added to a natural genetic micromorphological marker increases the number of related similar products that can be marked. The dye compounds can also provide a molecular signature should one require more than a rapid subjective examination.

Figure 2:
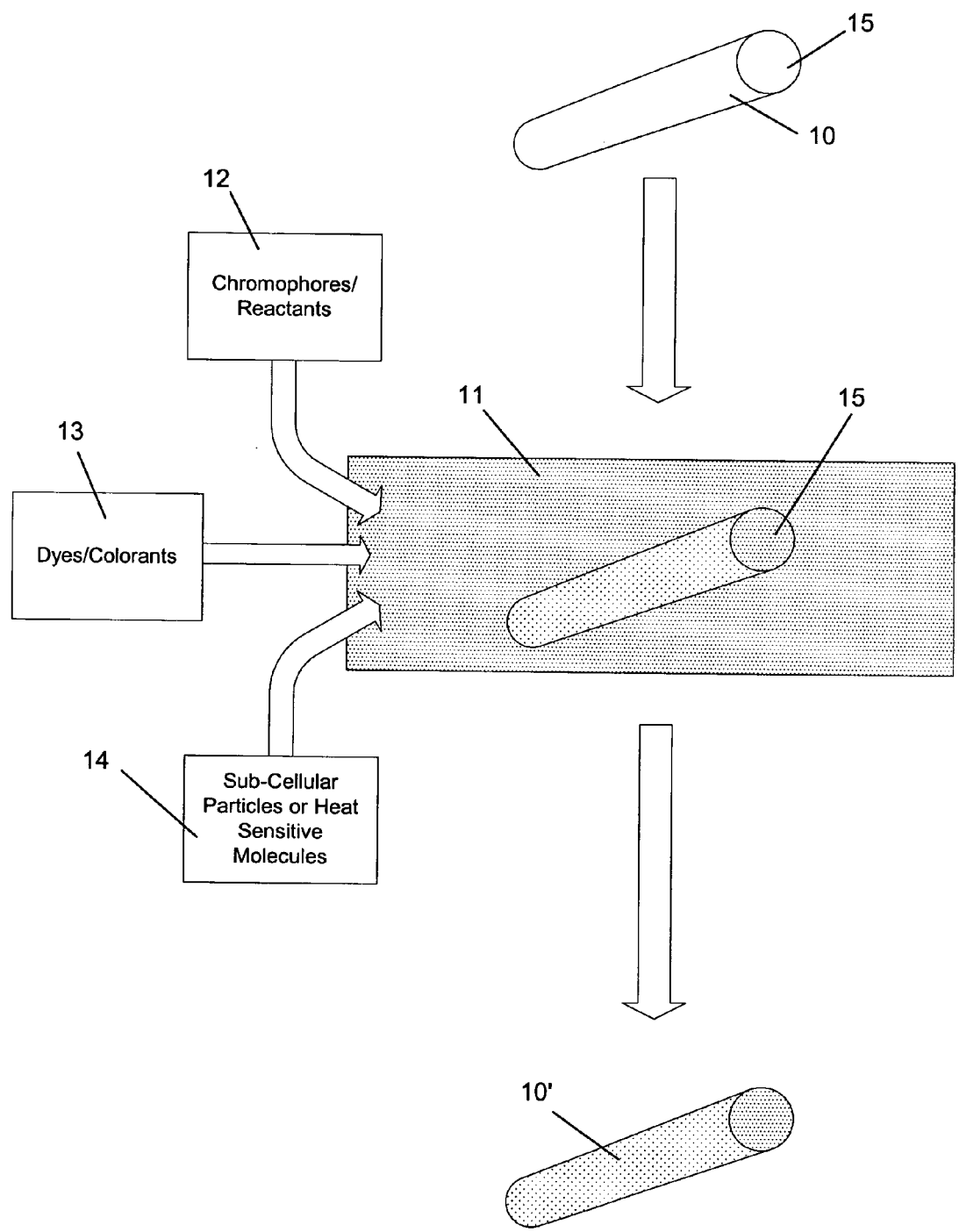
FIG. 2 is a diagram showing the process for making markers for food products using natural cellulosic plant material having hollow fibers according to the present invention.

As explained above, many of the natural cellulosic markers available for use in foods according to the present invention are hollow. The secondary dyes and reactants can be vacuum infused into the hollow interior spaces of the natural cellulosic markers where they are protected from subsequent processing. As depicted in FIG. 2, the hollow cellulosic material 10 is placed in a vacuum chamber 11 with the secondary marker materials 12, 13 and sub-cellular particles or heat sensitive molecules 14 (explained below) for a sufficient time and under a sufficient vacuum that the secondary marker materials 12, 13 and sub-cellular particles or heat sensitive molecules 14 infuse into the hollow interior spaces 15 of the cellulosic material 10. The infused cellulosic material 10' is then ready for use as a marker in a food product.

In other cases, the secondary characteristics provided by the dyes and reactants can be enrobed in or absorbed into carriers that can fill surface voids and pits and thereby remain secured in the marker structures until examined.

Molecular Thermometers

Sub-cellular particles or heat sensitive molecules 14 (FIG. 2) can be added to the natural micromorphological markers to provide a molecular thermometer for the marker. This is shown as step S5 in FIG. 1. For example, starch granules or enzymes can be vacuum infused into the hollow interior spaces or attached to the surfaces of the natural cellulosic markers. Starch granules that gelatinize at a temperature just below a process temperature can be used to provide an internal molecular thermometer to a cooking process that must reach a minimum temperature. Enzyme systems work in a similar way, have narrow ranges of denaturation (the point where they lose their activity), and can serve as molecular thermometers around a particular cook point temperature.

Both of these types of markers and other related cellular constituents can be selected to provide process control markers. Intact starch and its gelatinization can be observed with both bright field and polarized light microscopy. When they are inside a hollow marker or affixed to the marker surfaces, they add a temperature monitoring function to the marker.

Enzymatic markers inside the hollow natural markers are best found by incubating a small sample with the visualization reagent in a depression slide or small dish. The colored reaction products formed can be used to confirm the cook temperature depending on the denaturation or activity of the enzyme in a limited time period. The location of the enzyme activity within the hollow interior spaces of the natural cellular marker would confirm the marked product. Enzymes are very specific in their reactivity which adds considerable additional specificity to the markers and to the temperature monitoring aspect of the markers. The enzyme detection solutions used are preferably not present in any form in the food so that no confounding of results will occur. The markers would be colorless and would not be visible until incubated in a drop of the enzyme test reagent.

Using a natural hollow micro-fiber carrier system is particularly useful for enzyme systems used as fixed point molecular thermometers. In food products they would normally be used to monitor the cooking temperatures. However, a heat sensitive marker could also be used in an adhesive bandage to determine if that bandage had been present when a product allegedly containing the bandage was cooked. An enzyme system or an enzyme substrate (reactant) could be used to monitor the environments to which a food product had been submitted over a time frame that would include shipping, warehousing, and so forth.

Sample Preparation and Detection Techniques

The present invention uses the unique genetically controlled micromorphological structures found in living organisms as materials for marking, tagging, or tracing (collectively referred to herein as "marking") processed foods and various other products. These unique micromorphological markers can subsequently be found by rapid visual examinations of the marked products without costly or lengthy analyses. This visual examination is shown as step S7 in FIG. 1. Identification of a marker, tag or trace (collectively referred to herein as a "marker") is a simple "presence or absence" determination. It requires no quantifying.

Rapid microscopic examinations depend on minimal sample preparation and ease of observations. These are subjective methods that are "YES-NO" types of tests. Some sample preparation can enhance the examinations. For example, the examination of a natural cellulosic tubular marker in a baked matrix will require gelatinization of the starches in the crumb structure to allow rapid evaluations and to eliminate any confounding of the observations by the background polarized light from the starch. Gelatinizing the starch will destroy its polarized light interference with the natural cellulosic markers during an examination. This can be accomplished by heating a small amount of crumb structure from a marked baked product on a slide in a mounting medium containing chloral hydrate. Similarly, a crumb sample could be wetted with strong alkali and heated on a slide to gelatinize the starch. A third method of gelatinization would be heating the wetted crumb (in distilled water) from a baked product on a slide in a steam bath or autoclave to completely gelatinize the starch. Larger samples can be produced when destructive testing is permitted. These can be autoclaved or heated in alkali in a beaker followed by sampling for microscopic examinations.

Clearinghouse for Different Marker Combinations

The natural marker materials and secondary markers described above can be used in various combinations to provide several different markers for food products. This will allow different markers to be used to identify different food manufacturers or suppliers providing food products to the same restaurant or outlet. It will also allow different markers to be used to identify different lots from the same food manufacturer or supplier.

Figure 3:
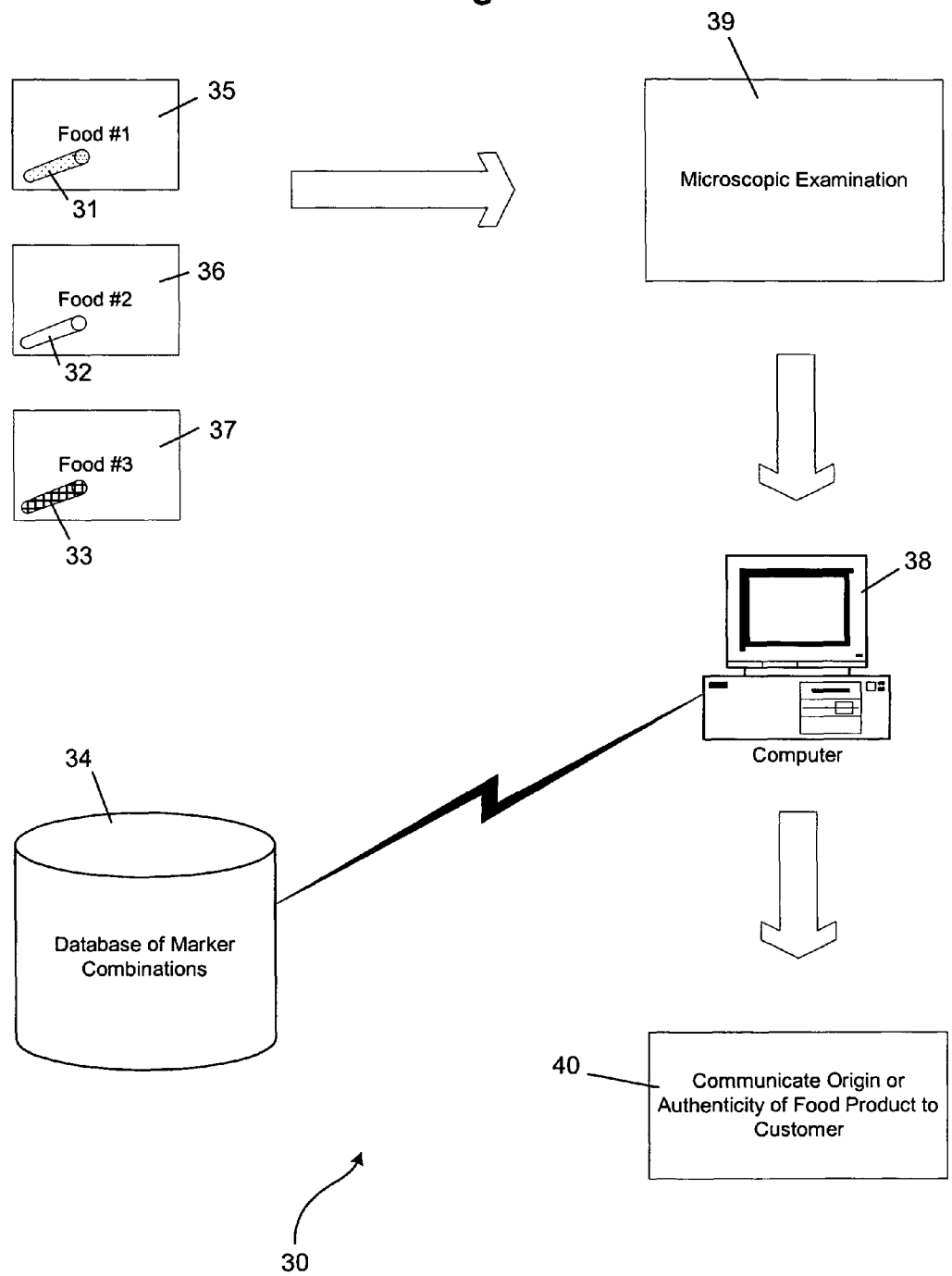
FIG. 3 is a diagram showing a clearinghouse arrangement for tracking and identifying several different marker combinations for food products.

As depicted in FIG. 3, a clearinghouse 30 for keeping track of the several different markers and marker combinations 31, 32, 33 can be provided using the concepts of the present invention. By combining different natural materials and different secondary markers (dyes and reactants), it will be possible to prepare dozens or even hundreds of distinctly different marker combinations that can be rapidly identified using microscopic examination. The clearinghouse 30 will have a database 34 containing a record of the different marker combinations 31, 32, 33 and information about the various food products 35, 36, 37 in which each such marker combination 31, 32, 33 has been used. A simple indexing system using a computer 38 will allow a product examiner at step 39 to match a detected marker combination 31, 32, 33 with a particular food product 35, 36, 37 or product source. The clearinghouse 30 can then offer the valuable service of supplying markers 31-33 to its corporate customers, collecting and storing information about how and where each marker is used, and matching such information with forensic samples of the food products 35-37. The clearinghouse 30 or an independent laboratory can perform the step 39 of examining forensic samples of the food products and using the computer 38 and database 34 to determine the origin or authenticity of the food product samples 35-37. This information can then be communicated to the corporate customer at step 40 and used as necessary to confirm or deny the origin or authenticity of the food product samples 35-37. This clearinghouse arrangement can also be used for tracking markers and marker combinations for nonfood products using the concepts of the present invention.

The following table illustrates a progression of eight different marker combinations that can be generated using a single natural cellulosic marker, two colors of dyes (e.g., food coloring), and two colors of chromophores. The dyes and chromophores can be infused into the hollow interior spaces of the natural cellulosic marker material using vacuum infusion or the other techniques described above before adding the marker material to the food product.

TABLE 1

Marker Combinations.

| Company | Natural Marker | Dye | Chromophore |
|---|---|---|---|
| 1 | Hollow Fiber #1 | Red | Brown |
| 2 | Hollow Fiber #1 | Red | Blue |
| 3 | Hollow Fiber #1 | None | Blue |
| 4 | Hollow Fiber #1 | None | Brown |
| 5 | Hollow Fiber #1 | Red | None |
| 6 | Hollow Fiber #1 | Yellow | None |

TABLE 1-continued

Marker Combinations.

| Company | Natural Marker | Dye | Chromophore |
|---------|----------------|--------|-------------|
| 7 | Hollow Fiber #1 | Yellow | Blue |
| 8 | Hollow Fiber #1 | Yellow | Brown |

An additional set of marker combinations can be produced by changing the natural fiber source. For example, a first set of marker combinations can be produced using sycamore seed fibers, and a second set of marker combinations can be produced using oat trichomes. Additional marker combinations can be produced, for example, by using two natural fiber sources in the same product (e.g., sycamore seed fibers and oat trichomes), and/or by using an additional reactant. The additional reactant can be selected so as not to interfere with any of the other reagents used in the detection technique. For example, the additional reactant can be a chromophoric reactant that can be heat activated to change color or pH activated to change color or be an entirely different enzymatic reaction, and so forth.

Experimental Examples

Several examples of the natural cellulosic plant material markers, secondary markers, molecular thermometers, and methods for preparing the markers have been given above. Specific working examples of the preparation of markers according to the present invention will now be explained.

The unique natural fibers from sycamore seeds were ground to reduce their length. These were blended into a sorbate-propionate food preservative mixture and micro-encapsulated with a fat soluble material. The concentration of marker to product was one part per million in order to verify that very low inclusion rates of markers could be used to confirm identities of products without any significant effects on a finished product. The low inclusion rate preservative was subsequently used to bake bread.

Tiny aliquots (less than 5 milligrams) of the bread were taken for examination. These sample aliquots were further prepared by heating a smaller sub-sample amount of the crumb structure from each sample on a slide in a mounting medium containing chloral hydrate to gelatinize the starch in the crumb structures. The sycamore fiber marker was unaffected by the hot mounting media, and the unique fibers were found in the bread at normal preservative rates. However, the extremely low inclusion rate of the preservative with only one part per million marker slowed the examination and confirmation process.

This experiment proved it was possible to locate unique cellulosic markers at extremely low concentrations in bread. It was possible to find the unique sycamore fiber markers at that concentration, but higher concentrations of markers in the low inclusion rate micro-encapsulated product would make it easier to identify the marked products (bread in this case) and speed up the examination process.

A second experiment to exploit the characteristics of these kinds of tiny hollow markers did not use baked products, but merely utilized the markers to prove the concept of making and handling micro-capillary products.

The natural marker material was the hollow cellulosic fibers from milkweed seeds. A small quantity of fibers was ground to reduce their fiber length and make them easier to mix. The fibers were placed in an aqueous red food color dye solution and a gentle vacuum drawn on the container to enhance the transfer of liquid into the micro-capillaries of the milkweed seed fibers. The fibers were subsequently rinsed to remove the excess colored dye and the liquid decanted. The dye in the hollow fibers remained inside the hollow fibers due to capillary forces.

The dye containing hollow fibers were placed in a ferrous salt solution. A gentle vacuum was applied to infuse the ferrous salt into the already dye-marked milkweed seed fibers. The fibers were rinsed to remove the surface absorbed reagent.

These markers were placed in an iron test solution consisting of potassium ferricyanide-potassium ferrocyanide solution (0.5 molar each for each component), and the fibers were examined after the excess iron reagent was rinsed off. The ferrous salt inside the hollow milkweed seed fibers reacted rapidly with the iron reagent to produce a readily seen insoluble indigo blue colored pigment inside the fiber. No iron reactions were observed on the outside of the fibers. This proved all the excess iron salt solution had been removed, and only the interior capillary fixed iron was reacting with the iron reagent. The indigo blue color was readily observed in the micro-capillary milkweed seed fiber tube along with the red food colorant dye. This also proved that multiple components—dyes, reactants, and enzymes—could be vacuum infused sequentially into the natural hollow fibers and then examined. Several mutually exclusive marker components could also be vacuum infused into the hollow fibers at the same time and used to modify the markers for several applications.

As explained above, the present invention is particularly suitable for marking food products and ingredients for food products. However, the concepts of the invention can also be used for marking a variety of other manmade products unrelated to the marker materials, including adhesive bandages, medicinal capsules, packaging materials, and various types of cleaning products.

While this invention has been described in relation to the preferred embodiments, it is to be understood that various modifications thereof will now be apparent to one skilled in the art upon reading this specification, and it is intended that all such modifications that fall within the scope of the following claims be covered by this application. The scope of the following claims should be construed as broadly as the prior art will permit.

What is claimed is:

1. A method of marking products, comprising the steps of:
   selecting a natural material having a unique genetically controlled micromorphological structure that can be identified using microscopic examination; and
   adding said natural material to a product unrelated to said natural material at a sufficiently low level so as not to have any significant effect on the product other than to serve as a marker for the product;
   obtaining a sample of the marked product; and
   determining by use of microscopic examination whether the sample contains said natural material;
   wherein said natural material is selected from the group consisting of cellulosic plant materials and sporopollenin.

2. The method according to claim 1, wherein said natural material is non-allergenic.

3. The method according to claim 1, wherein said natural material is selected to match characteristics and functional properties of the marked product.

4. The method according to claim 1, wherein said natural material is resistant to visible changes induced by mechanical, physical or chemical processing variables during manufacturing of the marked product.

5. The method according to claim 1, wherein said marked product is a food product.

6. The method according to claim 1, wherein said natural material comprises natural cellulosic plant material.

7. The method according to claim 6, wherein said natural cellulosic plant material is obtained from the group consisting of leaves, weed seeds, and cockle burrs.

8. The method according to claim 6, wherein said natural cellulosic plant material comprises plant hairs or other plant appendages.

9. The method according to claim 6, wherein said natural cellulosic plant material comprises hollow plant fibers.

10. The method according to claim 9, wherein said natural cellulosic plant material is selected from the group consisting of sycamore seed fibers, oat trichomes, milkweed pods, capok, and alfalfa trichomes.

11. The method according to claim 1, wherein said natural material comprises sporopollenin.

12. The method according to claim 11, further comprising the step of preparing said sporopollenin by removing surface antigens and active enzymes from pollen or other allergenic particles.

13. The method according to claim 1, further comprising the step of adding at least one reactant to the natural material.

14. The method according to claim 13, wherein said at least one reactant is a chromophoric reactant.

15. The method according to claim 1, further comprising the step of adding a colored compound to the natural material to create a secondary identifiable visual characteristic.

16. The method according to claim 15, wherein said colored compound is a dye.

17. A method of marking products, comprising the steps of:
selecting a natural material having a unique genetically controlled micromorphological structure that can be identified using an enhanced visualization technique; and
adding said natural material to a product unrelated to said natural material at a sufficiently low level so as not to have any significant effect on the product other than to serve as a marker for the product;
wherein said natural material has hollow interior spaces, and further comprising the step of vacuum infusing a secondary marker into said hollow interior spaces.

18. The method according to claim 17, wherein said secondary marker is selected from the group consisting of dyes and reactants.

19. The method according to claim 17, wherein said secondary marker is a metallic ion.

20. A method of marking products, comprising the steps of:
selecting a natural material having a unique genetically controlled micromorphological structure that can be identified using microscopic examination; and
adding said natural material to a product unrelated to said natural material at a sufficiently low level so as not to have any significant effect on the product other than to serve as a marker for the product;
obtaining a sample of the marked product; and
determining by use of microscopic examination whether the sample contains said natural material;
wherein said natural material has surface voids, and further comprising the step of securing a secondary marker within said surface voids.

21. The method according to claim 20, wherein said step of securing a secondary marker within said surface voids comprises placing the secondary marker in a carrier that fills said surface voids.

22. The method according to claim 21, wherein said secondary marker is placed in said carrier by enrobing or absorption into the carrier.

23. A method of marking products, comprising the steps of:
selecting a natural material having a unique genetically controlled micromorphological structure that can be identified using an enhanced visualization technique; and
adding said natural material to a product unrelated to said natural material at a sufficiently low level so as not to have any significant effect on the product other than to serve as a marker for the product;
further comprising the step of adding sub-cellular particles or heat sensitive molecules to said natural material to provide a molecular thermometer for the marker.

24. The method according to claim 23, wherein said step of adding sub-cellular particles or heat sensitive molecules comprises adding starch granules to said natural material.

25. The method according to claim 23, wherein said step of adding sub-cellular particles or heat sensitive molecules comprises adding enzymes to said natural material.

26. The method according to claim 23, wherein said sub-cellular particles or heat sensitive molecules are infused into hollow interior spaces of said natural material.

27. The method according to claim 23, wherein said sub-cellular particles or heat sensitive molecules are attached to a surface of said natural plant material.

28. A method of determining an origin or authenticity of a marked product, comprising the steps of:
obtaining a sample of the marked product;
determining by use of microscopic examination whether the sample contains a particular natural material having a unique genetically controlled micromorphological structure at a sufficiently low level so as not to have any significant effect on the marked product other than to serve as a marker for the product; and
comparing the detected natural material with an information record to determine the origin or authenticity of the marked product;
wherein said natural material is selected from the group consisting of cellulosic plant materials and sporopollenin.

29. A method of determining an origin or authenticity of a marked product, comprising the steps of:
obtaining a sample of the marked product;
determining by use of microscopic examination whether the sample contains a particular natural material having a unique genetically controlled micromorphological structure at a sufficiently low level so as not to have any significant effect on the marked product other than to serve as a marker for the product; and
comparing the detected natural material with an information record to determine the origin or authenticity of the marked product;
further comprising the step of determining whether the marker contains a particular visual characteristic indicating the presence of a secondary marker for the marked product.

30. The method according to claim 29, wherein said visual characteristic is a color.

31. The method according to claim 29, wherein said secondary marker is a starch or an enzyme located in a particular structure of the natural material, and further comprising the step of determining by observation of said secondary marker whether the marked product had reached a predetermined minimum temperature.

32. The method according to claim 29, wherein said visual characteristic is located in a particular structure of a natural cellulosic plant material.

33. The method according to claim 32, wherein said particular structure is a hollow interior space of the natural material.

34. A method of determining an origin or authenticity of a marked product, comprising the steps of:
 obtaining a sample of the marked product;
 determining by use of microscopic examination whether the sample contains a particular natural material having a unique genetically controlled micromorphological structure at a sufficiently low level so as not to have any significant effect on the marked product other than to serve as a marker for the product; and
 comparing the detected natural material with an information record to determine the origin or authenticity of the marked product; wherein said marked product is a food product containing starch, and further comprising the step of gelatinizing starch in the product sample before observing the sample using enhanced visualization to avoid confounding the observation by background polarized light from the starch.

* * * * *